US00PP18761P3

(12) United States Plant Patent
Braun

(10) Patent No.: US PP18,761 P3
(45) Date of Patent: Apr. 29, 2008

(54) APPLE TREE NAMED 'FUJI FUBRAX'

(50) Latin Name: *Malus domestica*
Varietal Denomination: Fuji Fubrax

(75) Inventor: Thomas Braun, Girlan/Eppan (IT)

(73) Assignee: Kiku SRL GmbH, Girlan/Eppan (IT)

( * ) Notice: Subject to any disclaimer, the term of this patent is extended or adjusted under 35 U.S.C. 154(b) by 0 days.

(21) Appl. No.: 11/355,401

(22) Filed: Feb. 16, 2006

(65) Prior Publication Data

US 2006/0185041 P1 Aug. 17, 2006

(30) Foreign Application Priority Data

Feb. 16, 2005 (EP) ..... 2005/0199

(51) Int. Cl.
*A01H 5/00* (2006.01)

(52) U.S. Cl. ..... Plt./168
(58) Field of Classification Search ..... Plt./168, Plt./162
See application file for complete search history.

(56) References Cited

PUBLICATIONS

D.C. Ferree, "Apples—Botany, Production and Uses" 2003, pp. 66–68, CABI Publishing.

*Primary Examiner*—Kent Bell
*Assistant Examiner*—S. B. McCormick-Ewoldt
(74) *Attorney, Agent, or Firm*—Horst M. Kasper

(57) ABSTRACT

The present invention relates to a variety of an apple tree obtained by branch mutation and by selection of the variety Fuji. The present invention variety exhibits an appropriate distinguishability, homogeneity, uniformity, and stability. The vigor of the tree is strong. The tree type is ramified. The habit of the apple tree is drooping. The pubescence on an upper half of a shoot is weak or similar to the pubescence in Golden Delicious. The thickness as measured by the diameter at the center is medium or similar to the thickness in Jonagold for a dormant one year old shoot. The number of lenticels is many for one year old dormant shoot. The color of an unopened flower is light pink in a balloon stage. The surface of the fruit is colored dark ruby red with a large number of small yellowish dots. Frequently the dots are disposed on curved lines with each line counting from about 4 to 8 dots.

4 Drawing Sheets

Latin name of the genus of the plant claimed: *Malus*.
Latin name of the species of the plant claimed: *Malus domestica*.
Variety denomination: 'Fuji Fubrax'.

BACKGROUND OF THE INVENTION

1. Field of the Invention

The present invention relates to a novel apple tree.

2. Brief Description of the Background of the Invention Including Prior Art

A known variety of an apple plant is *Malus domestica*. A variety of *Malus domestica* is called 'Fuji'. Another variety of *Malus domestica* is called 'Brak' or 'Fuji Brak' and is described in U.S. Plant Pat. No. 15,261.

BRIEF SUMMARY OF THE INVENTION

A vegetatively propagated variety of *Malus domestica* is designated as 'Fuji Fubrax'. The variety has been bred by a naturally occurring tree mutation of the variety 'Fuji' (not patented) by selection such that the variety 'Fuji Fubrax' exhibits necessary distinguishability, homogeneity, uniformity, and stability.

DETAILED BOTANICAL DESCRIPTION

Figure 1:
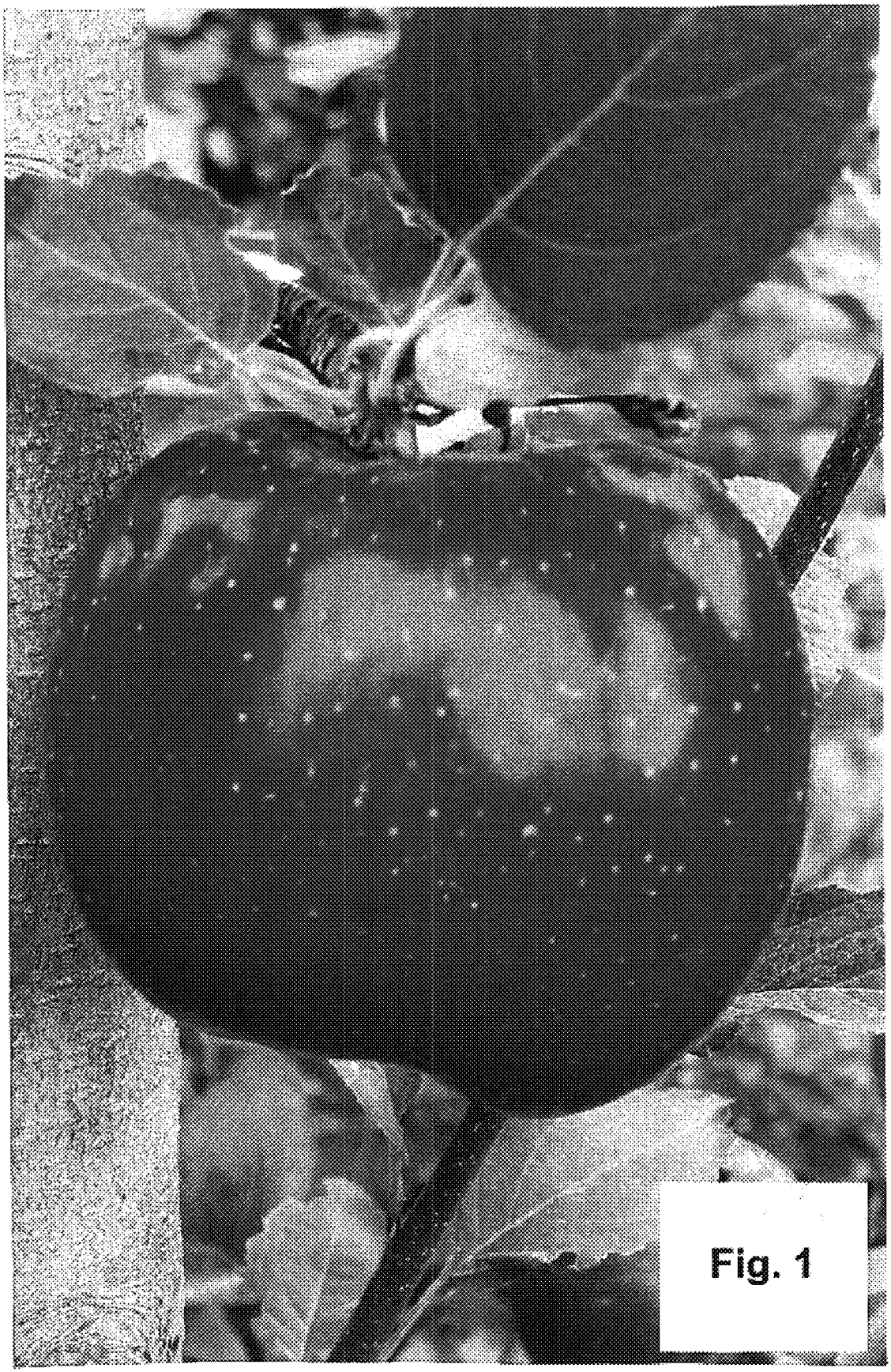
FIG. 1 is a front side elevational view of a fruit of the apple tree.
Figure 2:
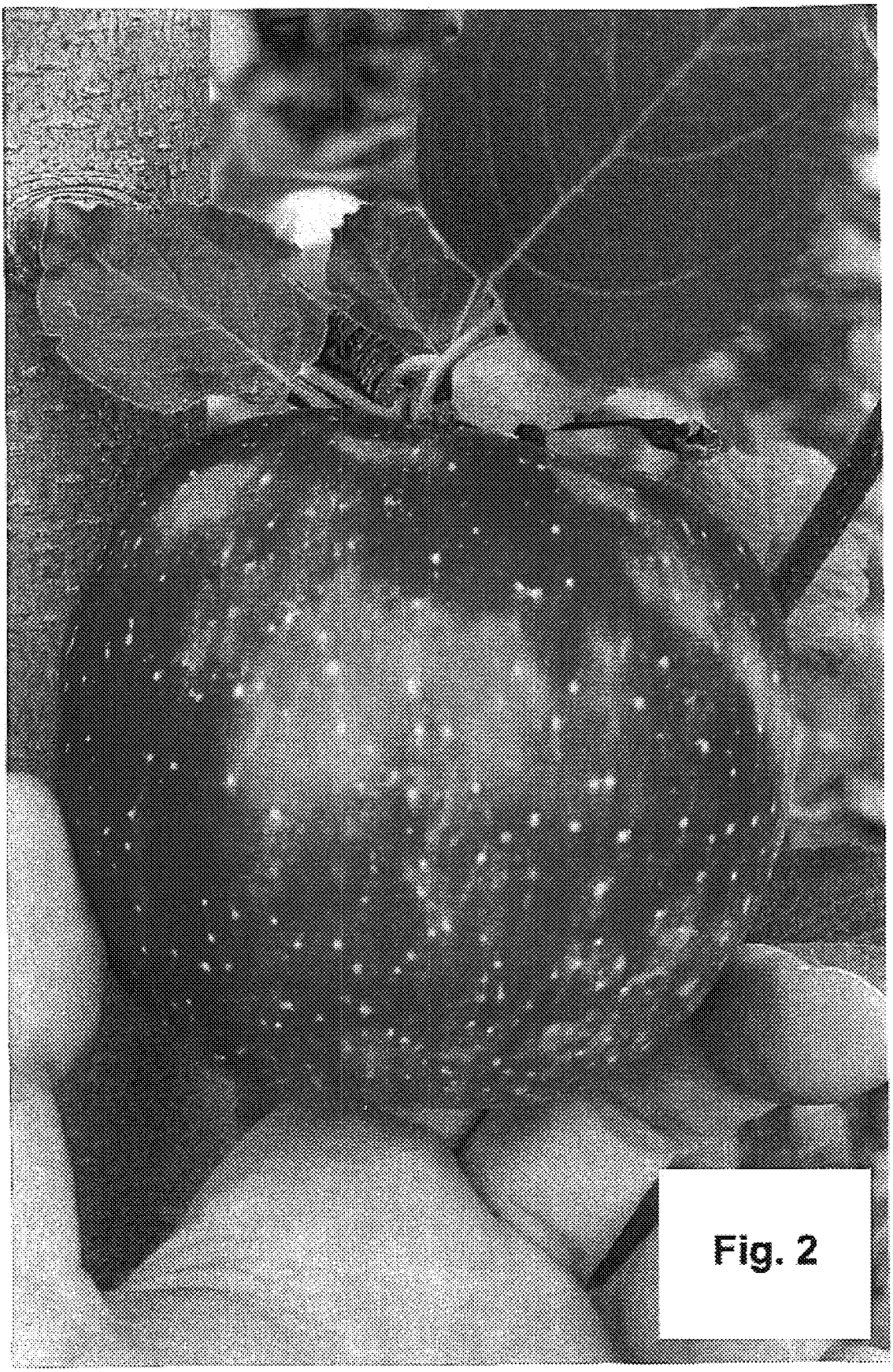
FIG. 2 is a back side elevational view of the fruit of the apple tree shown in FIG. 1.
Figure 3:
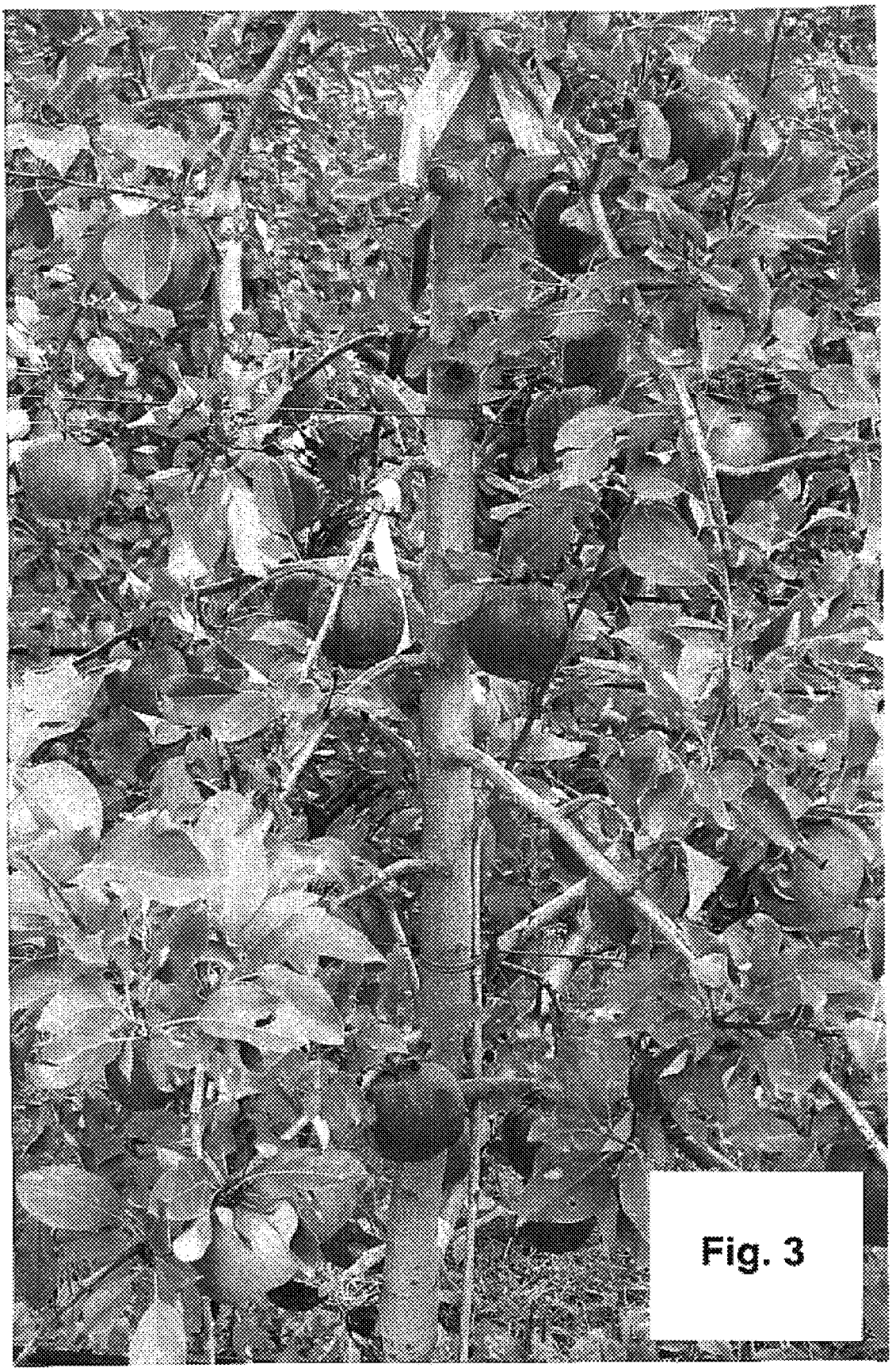
FIG. 3 is a side elevational view of fruits hanging on the apple tree.
Figure 4:
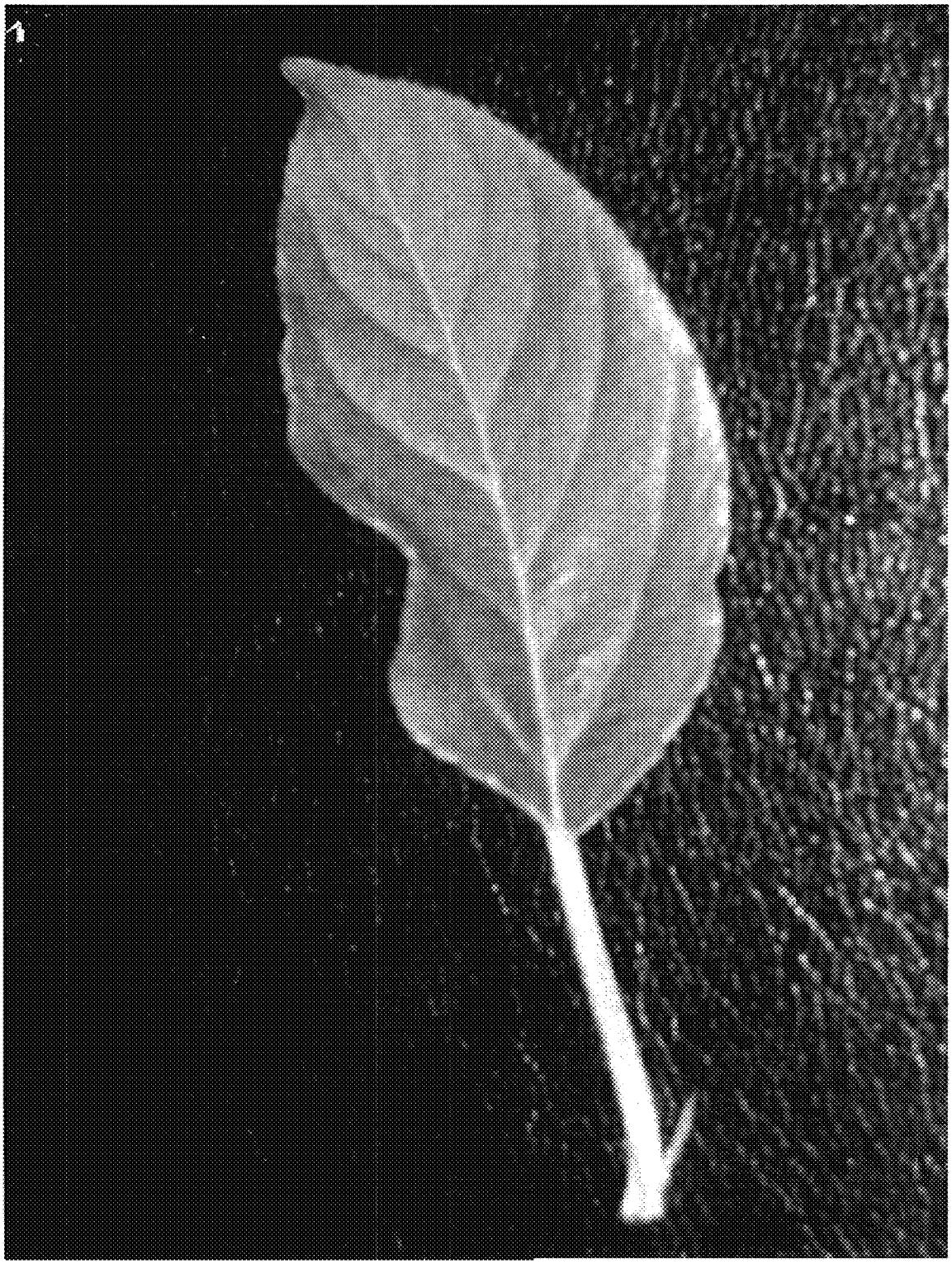
FIG. 4 is a top planar view of a leaf of a 'Fuji Fubrax' tree.

The present invention relates to a variety of an apple tree. A naturally occurring tree mutation of the variety 'Fuji' (not patented) has been discovered and found by selection such that the present invention variety exhibits an appropriate distinguishability, homogeneity, uniformity, and stability.

The stability of the propagation of the tree 'Fuji Fubrax' was monitored. The tree 'Fuji Fubrax' shows a 99 percent variety originality in commercial installations. The so-called regression rate or reversion rate is only 1 percent. The typical properties of 'Fuji Fubrax' have not changed in the course of propagation. The observed plant retains its distinctive characteristics and reproduces true to type in successive generations. 'Fuji Fubrax' is reproduced by chip budding. The original 'Fuji Fubrax' tree was found in the fruit plantation "Merol" located in the section GIRLAN of the community EPPAN in South Tyrol, Italy. The mother tree was planted in 1999. The first observations were made in the year 2002. The first propagation was performed in 2002. The first observations on the next generation were made in 2003. The asexual reproduction took place in a nursery in Verona in Northern Italy. The observations were made on the mother tree and with trees having an age from two to five years.

The vigor of the 'Fuji Fubrax' tree is strong and similar to the vigor of Gloster. The tree type is ramified. The habit of the 'Fuji Fubrax' apple tree is drooping. The pubescence on an upper half of a shoot is weak similar to Cox's Orange. The thickness as measured by the diameter at the center is medium and similar to Jonagold for a dormant one year old shoot. The length of the internode is medium and similar to Jonagold for a dormant one year old shoot.

The height of a one year tree is from about 1.7 m to 1.8 m. The height of a two year tree is from about 2.2 m to 2.5 m. The height of the trunk of a two year old tree is from about 75 to 80 cm. The length of the branches of a one year old tree is from about 30 to 50 cm. The diameter of the spread of a one year old tree can be from about 35 cm to 70 cm. The length of the branches of a two year old tree is from about 50 to 60 cm. The diameter of the spread of a two year old tree can be from about 60 cm to 85 cm. The angle of the branches of a one to two year old tree is from about 35 to 45 degrees. The angle of the branches of a 3 year old tree is from about 55 to 60 degrees. The diameter of the trunk of a one year old tree is from about 12 to 16 mm. The diameter of the trunk of a two year old tree is from about 25 to 30 mm.

The number of lenticels is many or similar to the number in Mutzu and Imperial Gala for a one year old dormant shoot.

The lenticels of the wood are clearly projecting, projections can be definitely felt upon palpating of the wood. Very many lenticels are present on the wood similar to the number of lenticels on the wood of Mutzu. The shape of the lenticels is dot like/circular up to globular/flattened. The lenticels on the trunk have a length of up to 2.2 mm and have a height of from 1 to 1.5 mm. In contrast, the lenticels on the branches are only from about 1.0 to 1.6 mm and are therefore smaller. The color of the lenticels on the trunk and on the branches is FAN4 155A to 155B. The Color Chart used in this specification is The Royal Horticultural Society Colour Chart.

Flower buds were observed on two year old shoots. The length of the flower buds was 5.8 mm. The width of the flower buds was 2.7 mm and this gives a length to width ratio of about 2:1. The diameter of the flower buds was 2.6 mm and their color was FAN4 183A.

The color of an unopened flower is light pink in a balloon stage similar to the color in Gravensteiner. The size of the flower as measured by the diameter of the flower with petals pressed into a horizontal position is medium or similar to the size of Cox's Orange. The petals have a length of about 20 mm and a width of about 13 mm. The ratio length to width of the petals can be from about 1 to 1.5. The petals of a flower are not overlapping. The diameter of a blossom is about 36 mm as seen from above. The relative position of the margin of the petals is touching. In most cases clusters of four or five blossoms are observed. No characteristic fragrance was observed at the blossoms.

The time of the beginning of flowering as measured by 10 percent open flowers is medium. The main flower on terminal buds had a flowering time of eight days. The duration of flowering of 'Fuji Fubrax' is the same duration as has 'Fuji'. The after flowering or in other words the time from the degradation of the blossom through the wilting and turning yellow of the blossom to the dropping of the petals of the blossom to the ground on one year old wood lasted 10 days. Once the tree starts flowering, it flowers regularly each year.

The properties of the flowers of 'Fuji Fubrax' are: The number of the petals is five. The length of a petal is about 20 millimeters+−2 millimeters. The width of a petal is about 13 millimeters+−1 millimeter. The ratio of length of a petal to width of a petal is about 1 to 1.5. The diameter of a flower as seen from above is about 36 millimeter+−2 millimeter. The petals have light veins and are delicately subdivided. The color of the petal in the balloon state is light pink and on the outside FAN2 47A-47B.

The upper side of the petals is colored white and the lower side of the petals is colored light pink. The petals of the open flower exhibit a color FAN4 WHITE N155D plus slight traces of FAN2 47A-47B on the outside. The petals of the open flower exhibit a color FAN4 WHITE N155D on the inside. The vessels of the pistil are erect and number from 10 to 12.

The reproductive organs have a length of from 5.1 to 9.8 millimeter.

The dehisced anther showed a color FAN4 160A. The undehisced anther showed a color FAN4 160C. The filament comprised 15 to 20 pieces with a length of from 0.51 to 0.98 cm. The color of the filament was FAN4 193D. The pollen had a color FAN4 160A.

The peduncle has a length of 17 to 20 millimeter and exhibits a color FAN3 GREEN 138B.

The observed variety is not self-fertile and not partially self-fertile and pollinators compatible would be Gala, Golden Gem, Evereste, Prof. Sprenger. No pollinators have been encountered, which are incompatible with the observed variety.

The flowers are average sensitive and average resistant against unfavorable weather conditions and freezing. The time of flowering is from April 10 to April 25 in South Tyrol depending on the climate.

The attitude of the leaf relative to the shoot is outwards. The length of the leaf blade is medium or similar to the length in Cox's Orange. The width of the leaf blade is medium or similar to the width in Jonagold. The ratio length to width of the leaf blade is medium or similar to the ratio in Jonagold.

The incisions of the margins of the leaf blade are serrated. The broad leaves disposed near the stem have 30 to 40 serrations on each of the two sides of the leaf. The elongated leaves disposed in the end regions of the shoots have about 50 serrations on each of the two sides of the leaf and a total of about 100 serrations for the whole elongated leaf. The length of the petiole is medium or similar to the length in Jonagold. The color of the petiole is FAN3 GREEN 138B. The length of a leaf of a two year old tree is 8 cm. The length of a leaf of a five year old tree is 9.5 cm. The width of a leaf of a two year old tree is 4.5 cm. The width of a leaf of a five year old tree is 6 cm. The ratio of length to width of a broad leaf disposed near the stem of a two year old tree is from about 1.6 to 1.8.

The length of a petiole or leafstalk of a two year old tree is from about 2.6 to 3.6 cm. The edges of the leaves of the 'Fuji Fubrax' apple tree are serrated. The edge of the broad leaves disposed near the stem of a two year old tree is serrated with about 60 to 80 points total for a broad leaf.

The leaves of 'Fuji Fubrax' have the following properties: The color of the top side of the leaf is FAN3 137A to 137B for younger trees. The color of the top side of the leaf is very dark FAN3 139A for older trees. The color of the bottom side of the leaf is FAN3, 137C to 138A for younger trees.

The color of the bottom side of the leaf is 137C for older trees The edge of the leaf is serrated. The number of serrated points is from 30 to 40. The ratio of the length to the width of a broad leaf disposed near the stem is from 1.5:1 to 1.6:1. The ratio of the length to the width of an elongated leaf disposed in an end region of a shoot is about 2:1. The leaf has veins and there are on each side of the leaf 6 veins. The veining of the leaves is pinnate. The venation pattern of the leaves is 45 degrees. The color of the veins on the bottom side of the leaf is FAN1 47B, the color is lighter toward the upper side up to FAN4 155B. The ratio of the length of the leaf (without petiole) to the length of the petiole is 2.2 to 2.5:1. The transition from the wood to the leaf has the color FAN4 178A.

The size of the fruit is large or similar to the size of the fruit of Mutzu. The ratio of height to width of the fruit is medium or similar to the ratio in Jonagold. The position of the maximum width of the fruit is toward the stem or pedicel. The shape of the fruit is globose. The prominence of ribbing of the fruit is absent or very weak. The crowning at the calyx end is absent or very weak.

The aperture of the eye or the calyx depression of the fruit is partly open similar to the aperture in Cox's Orange. The size of the eye or calyx depression of the fruit is medium or similar to the size in Cox's Orange. The depth of the eye basin or calyx depression is deep or similar to the depth in Golden Delicious. The width of the eye basin or calyx depression is broad or similar to the width in Golden Delicious. The depth of the stalk cavity or stem cavity of the fruit is medium or similar to the depth in Bramley's seedling. The width of the stalk cavity of the fruit is medium or similar to the width in Golden Delicious. The opening of the cavity of the stem of an apple of a two year old tree is from about 2 to 2.5 mm. The opening of the cavity of the calyx of a fruit from a two year old tree is from about 2 to 2.5 mm.

The thickness of the stem or pedicel of the fruit is medium or similar to the thickness in Cox's Orange. The diameter or thickness of the stalk or stem of an apple of a two year old tree is from about 1.5 to 2 mm. The length of the stem or pedicel of the fruit is long or similar to the length in Richared Delicious. The length of a stalk of an apple of a two year old tree is from about 1 to 2 cm.

The visual length of the sepal of the fruit is medium or similar to the visual length in Champion.

The relief of the surface of the fruit is smooth or similar to the relief in Bramley's Seedling. The bloom of the skin of the fruit is absent. A greasiness of the skin of the fruit is absent. The color of the ground color of the skin of the fruit if visible is green yellow. The color of the over color of the skin of the fruit is dark ruby red striped. The intensity of the color of the over color of the skin of the fruit is dark. The amount of over color of the skin of the fruit is extremely high (90 percent). The pattern of over color of the skin of the fruit is blush-striped (faded-striped). These are the most evident differences of the fruit relative to the fruits of other Fuji strains: The fruit of Fuji Fubrax shows some weeks earlier coloration relative to the fruit of other Fuji strains, shows very high over color, shows striped coloration on the side of the fruit not exposed to the sun, and Fuji Fubrax fruit grown in the shadow part of the tree exhibits very high over color and stripes around the fruit. The amount of russet around are the eye basis or calyx depression of the fruit is absent or very low. The amount of russet on the cheeks of the fruit is absent or very low. The amount of russet around the stalk cavity or stem cavity of the fruit is low like in Elstar. The size of the lenticels of the fruit is medium or similar to the size in Cox's Orange.

The firmness of the flesh of the fruit as measured with a penetrometer is firm like the fruit of a Fuji tree. The color of the flesh of the fruit is yellowish. The aperture of the locules for a median through locules of the fruit in cross-section is partly open and similar to the aperture in Reine de Renettes.

The time of fruit ripening for eating is late.

The surface of the fruit is colored dark ruby red with a large number of small yellowish dots. Frequently the dots are disposed on curved lines with each line counting from about 4 to 8 dots. The diameter of the dots is generally less than 0.5 mm and nearly always less then a millimeter. The total number of dots is estimated to be between from about five hundred to five thousand for a single fruit.

The lenticels of the fruit are present in a high number of from about 5 to 8 per $cm^2$ without forming a pattern. The diameter of the lenticels of the fruit are from about 0.6 mm to 1.1 mm.

The number of lenticels increases in a direction toward the hollow of the calyx to 10 to 14 per $cm^2$ and the size of the lenticels decreases to from about 0.4 to 0.6 mm. The color of the lenticels of the fruit is FAN4 160B. The time of duration from the flowering to the harvest is from about 170 to 180 days. 'Fuji Fubrax' is sensitive to the plant disease scabs. Diseases of the fruit include glassiness such as water core or honey core in case of over ripeness or, respectively, in case of a delayed harvest, which is a general problem of the varieties 'Fuji'. The apple 'Fuji Fubrax' has from about 8 to 12 kernels. Many chambers contain two kernels. The length of the kernels is from about 9.5 to 9.9 mm. The width of the kernel at the widest point is about 5.5 mm, which occurs at a distance of a third from the heart of the kernel. The width of the kernel at about two thirds of a distance from the heart of the kernel is about 3.5 mm. The thickness of the kernel of 'Fuji Fubrax' is from about 2.8 to 3 mm. The color of the kernel is FAN4 166C. Stripes or areas with darker color are present at the edges of the kernels and exhibit a darker color FAN4 166A to 166B. The interior of the kernel shows the color FAN4 155B.

The colors of the written description override the colors of the pictures. The colors were compared with The Royal Horticultural Society Color Chart as follows:

The bottom side of a leaf had the color FAN3, 137C.

The top side of a leaf had the color FAN3, 139A. The trunk of two year old trees had the color FAN4, N200B. The trunk of five year old trees had the color FAN4, N200C. The branches of the trees had the color FAN4, N200C. The lenticels of the trees had the color FAN4, 198D. The base color of the apple was FAN3, 144D. The color of the striping of the apple was FAN1, 45A. The color of the flesh of an apple fruit was FAN1, 13D. The color of the stalk or pedicel of an apple was FAN3, 144D. The color of a closed flower was FAN, N67C. The color of an open flower was FAN4, N155A. The color of the seeds was FAN4, 1663. The color of the cavity of the calyx was FAN3, 145A. The color of the cavity of the stalk or stem cavity was FAN3, 145A. Two year old trees 'Fuji Fubrax' were observed at 30 cm away from the grafting location to have the color FAN4 177A and 130 cm away from the grafting location to have the color FAN4 177*a* to 177B. This means that during a young phase of the 'Fuji Fubrax' tree trunk and branches have the color FAN4 177A. The trunk and the old branches assume the color grey (FAN4 201C) more and more with increasing age, while the young wood (one to two years old) of the branches retains the color FAN4 177A.

A comparison was performed between 'Myra (U.S. Plant Pat. No. 9,845) and 'Triple E' (U.S. Plant Pat. No. 12,219) and 'Fuji Fubrax'. An immediate comparison is difficult, since the climatic conditions are different and the environmental conditions are different. The color indications for 'Fuji Fubrax' and 'Triple E' are based on the R.H.S. color chart, the color indications of 'Myra' are based on the Munsell color code. The covering color of the 'Fuji Fubrax' was dark Ruby red (45A). The covering color of 'Myra' was pinkish red 39-12 to 39-13. The covering color of 'Triple E' was Red 53B. The striping of 'Fuji Fubrax' was uniform and not too wide. The striping of 'Myra' was slightly darker with pinkish-red stripes. 'Triple E' did not exhibit any stripes. The color development of the apple 'Fuji Fubrax' occurred early, some weeks before 'Fuji'.

The color development of the apple 'Myra' occurred 14 days earlier than that of standard 'Fuji' and there were red striped strains. Apples of the 'Fuji Fubrax' tree color some weeks before standard Fuji and Myra apples and the first which is evident are stripes appearing on the 'Fuji Fubrax' apples. The fruit maturation of 'Fuji Fubrax' was homogeneous. One can harvest all the crop of 'Fuji Fubrax' in a first picking because of uniform apples and because all 'Fuji Fubrax' apples have the same properties. Even those apples in the shadow areas of the tree and all apples 'Fuji Fubrax' have the same properties over the complete surface of the apple. This is associated with some advantages including a maximum of two pickings, uniform apples, better storage properties.

The fruit maturation of 'Myra' apples was seven days earlier than the fruit maturation of red striped strains. The fruit maturation of 'Triple E' apples was 10 to 14 days before "BC2". The 'Triple E' apples growing in the shadow are more of a yellow green color (154C). The color of the 'Fuji Fubrax' leaves is very dark (139A). The color of the 'Myra' leaves is (21-14). The color of the 'Triple E' leaves is (138A). The ratio of the length to the width of the 'Fuji Fubrax' leaves is about 1.6:1 and the leaves are broad. The length of the 'Triple E' leaves is 8.4 cm and the width of 'Triple E' leaves is 3.2 cm. The color of the flesh of the 'Fuji Fubrax' apple fruit was (158A). The color of the flesh of 'Triple E' was (158D to 155D).

Comparison of the properties of 'Fuji Fubrax' with those of 'Fuji' apples: The point in time of flowering for 'Fuji Fubrax' is the same as the time of flowering of 'Fuji'. The growth speed of 'Fuji Fubrax' is the same as the growth speed of 'Fuji'. The leaf color of 'Fuji Fubrax' apples is dark green. The leaf color of 'Fuji Fubrax' is light green. The leaf size of 'Fuji Fubrax' is large, the leaf size of 'Fuji' is medium. The tree habit of 'Fuji Fubrax' shows steep sticks. The tree habit of 'Fuji' shows more flat sticks. The vigor of the 'Fuji Fubrax' tree is strong. The vigor of the 'Fuji' tree is medium. The size of the lenticels on wood of the 'Fuji Fubrax' tree are large. The size of the lenticels on wood of the 'Fuji' tree are medium. The color of the flesh of the fruit of 'Fuji Fubrax' is yellow. The color of the flesh of the fruit of 'Fuji' is white green. The color of the over-color of the skin of the 'Fuji Fubrax' fruit is brightly dark ruby-red. The color of the over-color of the skin of the 'Fuji' fruit is slightly orange-red. Coloration of the fruit of 'Fuji Fubrax' begins to show some weeks earlier than coloration of the fruit of Fuji. The pattern of the over-color of the skin of the 'Fuji Fubrax' fruit is blush striped. The pattern of the over-color of the skin of the 'Fuji' fruit is washed out-striped. The amount of the over color of the skin of the 'Fuji Fubrax' fruit is very high including in the shadow zone. The amount of the over-color of the skin of the 'Fuji' fruit is medium and in the shadow zone the color is green. The brix of 'Fuji Fubrax' shows a high amount of sugar. The brix of 'Fuji' shows a lower amount of sugar. The percentage of salable fruits of 'Fuji Fubrax' is high (95 percent). The percentage of salable fruits of 'Fuji' is medium (40 percent).

The fruits of 'Fuji Fubrax' growing up in the shadow are colored red. The fruits of 'Fuji' growing up in the shadow are colored green. A characteristic feature of the tree 'Fuji Fubrax' relative to the tree 'Fuji' is the ruby-red color of the fruit and the stripes of 'Fuji Fubrax'. All apples of the variety 'Fuji Fubrax' are colored over their complete surface, even those located in the shadow region of the tree. Particularly remarkable is the coloration of the 'Fuji Fubrax' apples in the cavity of the calyx and in the cavity of the stalk or stem cavity of the apples. Also, 'Fuji Fubrax' develops the red over color some weeks before Fuji. Based on these features of the 'Fuji Fubrax' apples, there is one picking and a maximum of two pickings of the apples. The first picking harvests the largest part of the fruits. The harvest of the 'Fuji Fubrax' apples occurs with optimum inner values of the 'Fuji Fubrax' apple. The 'Fuji Fubrax' apple has a higher percentage of uniform and marketable product as compared to 'Fuji' apples. The 'Fuji Fubrax' apple exhibits a better storage behavior and for example less water core and less brown coloring of the fruit flesh as compared with 'Fuji' apples. The shelf-life of the 'Fuji Fubrax' apple is extended relative to the shelf-life of 'Fuji' apples. There is less rust formation and russet with 'Fuji Fubrax' apples as compared with 'Fuji' apples. It is another characterizing feature of the 'Fuji Fubrax' apple tree that the apples color very early on the tree as compared to the variety 'Fuji'. In a tree nursery, the 'Fuji Fubrax' tree has better rates of grafting in the course of asexual propagation, exhibits a stronger growth and a more uniform growing in comparison with a 'Fuji' tree. 95 percent of the fruits are harvested in the first picking with 'Fuji Fubrax' trees. The part of uniformly looking and therefore marketable apples is higher as compared to 'Fuji'; from 65 to 75 percent of the apples are of a size from 80 to 90 mm. All 100 percent of the 'Fuji Fubrax' apples are of good color. 'Fuji Fubrax' can be harvested at an optimum point in time of harvesting. 'Fuji Fubrax' has reached the highest coloration of the covering color at that point in time, where the scientifically determined optimum and ideal internal values of the fruit (pressure, sugar, acidity, starch) have been reached. This is in contrast to the case with 'Fuji'; the 'Fuji' apples have to hang for a longer time on the tree, surpass the ideal harvesting values and therewith the optimum point in time of harvesting until the 'Fuji' apple reaches a red coloration. 'Fuji Fubrax' apples exhibit during storage less damages such as water core and brown discoloration of the flesh based on the optimum harvesting point in time, the 'Fuji' apples in comparison exhibit a higher water core. 'Fuji Fubrax' apples are not so rusted or russeted on the tree as are 'Fuji' apples.

The ruby-red covering color of the 'Fuji Fubrax' apples develops very early on a comparative scale with 'Fuji' apples. The component of covering color of 'Fuji Fubrax' apples is at about 95 percent about twice as high as is the case with standard 'Fuji' apples.

The lenticels of 'Fuji Fubrax' on the wood of the trunk and of the branches are particularly characterizing and clearly distinguish a 'Fuji Fubrax' tree from a 'Fuji' tree. The leaves of the 'Fuji Fubrax' tree are darker as compared to the leaves of the 'Fuji' tree.

The observed color of the over-color of 'Fuji Fubrax' apples is lightly ruby-red. The amount of color of over-color of the skin is very high, also the back sides of the 'Fuji Fubrax' apples are well colored. Even 'Fuji Fubrax' apples in the shadow zone of the tree are colored. Even though the 'Fuji Fubrax' apples are almost 100 percent colored, the apples still show stripes.

Coloration of the fruits begins some weeks earlier than in normal 'Fuji'. Six weeks before harvesting time, 'Fuji' apples are still almost green, while 'Fuji Fubrax' apples are nicely colored up to 50 percent.

I claim:

1. New and distinct variety of a 'Fuji' apple tree substantially as herein shown and described.

* * * * *